United States Patent [19]

Clifford, Jr.

[11] Patent Number: 5,370,126
[45] Date of Patent: Dec. 6, 1994

[54] METHOD AND APPARATUS FOR THREE-DIMENSIONAL MAPPING OF EVOKED POTENTIALS

[75] Inventor: James O. Clifford, Jr., Redwood City, Calif.

[73] Assignee: Neurotech, Inc., Whitefish, Mont.

[21] Appl. No.: 35,911

[22] Filed: Mar. 23, 1993

Related U.S. Application Data

[63] Continuation of Ser. No. 923,817, Jan. 22, 1992, abandoned.

[51] Int. Cl.$^5$ .............................................. A61B 5/04
[52] U.S. Cl. ............................ 128/731; 364/413.05; 364/413.13
[58] Field of Search ............... 128/731, 732, 733, 745, 128/746; 364/413.02, 413.05, 413.13

[56] References Cited

U.S. PATENT DOCUMENTS

| | | | |
|---|---|---|---|
| 4,736,307 | 4/1988 | Salb | 364/518 |
| 4,913,160 | 4/1990 | John | 128/731 |
| 4,955,388 | 9/1990 | Silberstein | 128/731 |
| 4,974,602 | 12/1990 | Abraham-Fuchs et al. | 128/731 |
| 5,003,986 | 4/1991 | Finitzo et al. | 128/731 |
| 5,010,891 | 4/1991 | Chamoun | 128/731 |
| 5,023,783 | 6/1991 | Cohen et al. | 364/413.02 |

FOREIGN PATENT DOCUMENTS 2234654  2/1991  United Kingdom ................. 128/731

OTHER PUBLICATIONS

Lim et al "A Practical Method . . . Analysis" IEEE. Transactions. vol. BME 27, No. 4. Apr. 1980.
Attias et al., *Electroencephalography and clinical Neurophysiology* (1990) 77:127–133 "Three-Channel Lissajous' . . . stimuli".
Donchin, "Evoked Brain Potentials and Behavior" (1979) H. Begleiter (Ed.), New York, New York, pp. 13–75.
Gardi et al., *Electroencephalography and clinical Neurophysiology* (1987) 68:360–367 "The 3—Channel Lissajous' . . . cat".
Jewett et al., *Electroencephalography and clinical Neurophysiology* (1987) 68:323–326 "The 3—Channel Lissajous' . . . response".
Martin et al., *Electroencephalography and clinical Neurophysiology* (1987) 68:327–332 "The 3—Channel Lissajous' . . . response".
Pratt et al., *Electroencephalography and clinical Neurophysiology* (1983) 56:682–688 "Three—Channel Lissajous' . . . potentials".
Shah, *Electroencephalography and clinical Neurophysiology* (1987) 68:409–411 "The 3—Channel Lissajous' . . . sequences".
Williston et al., *Brain Research* (1981) 223:181–184 "Planar curve analysis . . . report".
Witt et al., *IFEE Transactions on Biomedical Engineering* (1989) 36(2):291–295 "Vector Analysis . . . Dipoles".
Scherg et al., *Electroencephalography and clinical Neurophysiology* (1985) 62:32–44 "Two bilateral sources . . . model".
Scherg et al, *Electroencephalography and clinical Neurophysiology* (1986) 65:344–360 "Evoked Dipole source . . . cortex".
Sininger et al, *Electroencephalography and clinical Neurophysiology* (1987) 68:368–379 "The 3—Channel Lissajous' . . . response".
Van Schellong, *Methode. Lin. Wschr.* (1938) 17:453–457.
Von Schellong et al., *Archiv. Kreislaufforschung* (1937) 2:1–17.

*Primary Examiner*—Ralph A. Lewis
*Assistant Examiner*—Guy V. Tucker
*Attorney, Agent, or Firm*—Paul R. Schenck; William H. Benz

[57] ABSTRACT

Coordinating stimuli generation and response signal processing provides for a real-time display of the stimuli response in a three-dimensional coordinate system and allows to select immediately the most appropriate evaluation programs for further processing of sensory information.

8 Claims, 3 Drawing Sheets

METHOD AND APPARATUS FOR THREE-DIMENSIONAL MAPPING OF EVOKED POTENTIALS

This application is a continuation of application Ser. No. 07/923,817, filed Jan. 22, 1992, now abandoned.

FIELD OF THE INVENTION

This invention relates to the representation of human and non-human electrophysiological signals recorded non-invasively from the scalp, amplified, translated into digital format, averaged, graphed and stored for statistical and diagnostic purposes in real time.

The apparatus and method of the present invention can be used as a diagnostic tool for stroke, hematoma, tissue damage to the brain, tumor (neurological), visual impairment, auditory impairment, somatosensory impairment, coma, head injury (open, closed), learning disability, schizophrenia, alcohol and drug related illness, neurological development, mental retardative impairment, autism, anoxia, associative inability to discriminate stimuli, Alzheimer's disease, and mental illness.

BACKGROUND OF THE INVENTION

Many types of neural function diagnostic tools exist at present. The CAT, PET (position emission test) and MRI (magnetic resonance imagery) all serve useful purposes as tools for measuring locations of impairment known to exist through gross symptomology. For example, MRI is used to access damage and reconstruct the area associated with a trauma. CAT and PET scans both reconstruct affected areas associated with a functional impairment. However, none of these devices are capable of doing real-time processing and imaging of actual processing of stimuli response information and related electrical phenomena. MRI, CAT and PET scans are tools designed to investigate static phenomena by means of off-line procedures. All three of these examination methods serve as different means of trying to locate and identify areas of concern. However, none of these means diagnoses the flow of activity or level of functional impairment through these areas as defined by normal electrical activity.

An increasing awareness has grown in the medical field about the need to be able to access not only static responses but also dynamic responses to actions and stimuli. Evaluation of dynamic responses can only be achieved with the ability to do real time diagnostic and real time imagery of electrophysiological events. Also, the ability to do real time mapping of the brain's electrical response will allow the medical field to observe dynamic events in both neurophysiological and neuroanatomical realms in real time. This ability will allow both clinicians and researchers to have a tool to examine and diagnose those phenomena which occur between the onset of incident or trauma and that time when the patient would normally have a more traditional examination of the insult. The present invention will focus on the process underlying the infliction, as well as show those areas affected by the trauma in a dynamic three-dimensional format.

SUMMARY OF THE INVENTION

The present invention utilizes the brain's natural electrical response to sensory stimuli and by recording, maps those areas of the brain exhibiting electrical activity.

Three pairs of electrodes, normal convex electrodes available from any medical supply, are attached to the head of the subject under examination via tape or by wearing a cap with electrodes embedded. The electrode pairs are as follows:

1) top of head to anterior throat
2) inion-nasion
3) left to right mastoid (behind ear).

A ground electrode is located at an inactive site of the upper part of the vertebral column. The electrodes are connected to differential amplification devices as disclosed below. Because the electrical charges of the brain are so small (on the order of microvolts), amplification is needed. The three amplified analog signals are converted to digital signals and averaged over a certain number of successive digital values to eliminate erroneous values originated by noise on the analog signal.

All steps defined above are linked to a timing signal which is also responsible for generating stimuli to the subject. The responses are processed in a timed relation to the stimuli and averaged as the brain responds to these stimuli. Of special interest are the responses within certain time periods and time instances after the occurrence of a stimulus of interest. These time periods and instances and their references are:

25 to 60 milliseconds: P1–N1
180 to 250 milliseconds: N2
100 milliseconds: N100
200 milliseconds: P2
300 milliseconds: P300

Stimuli can be presented via any sensory modality, at any rate, and any probability. The probability of the presentation determines the amplitude of the brain's response.

In an examination two stimuli sets may be used in a manner that the brain has to respond to the two stimuli differently, one stimulus has a high probability of occurrence, and the other stimulus is a rare occurring phenomena. The rare response is the response of importance.

Three response signals are sensed and joined into a three dimensional cartesian system by a mapping program. The assignments are (see FIG. 1):

nasion−inion=X,
left−right mastoid=Y, and
top of head to anterior throat=Z.

The assignment of the probes to the axes and the simultaneous sampling of the three response signals at the same rate and time relative to the stimuli allows to real-time map the electrical phenomena in a three dimensional space. Depending upon the selected graphic display program the electrical phenomena can be displayed in a perspective representation of the three dimensional space, or the three components of the vector are displayed by projecting the vector onto the three planes X-Y, Y-Z, and X-Z, and the three planes are inspected together or separately. FIG. 3 is an illustration of a trajectory of 15 successively measured response vectors in a perspective 3-D display. The gathered information lacks the necessary distance from 0,0,0 axis information, however. In order to define the distance between the response and the origin of the coordinate system, one needs to combine the signal amplitudes in the following manner defined as Vector Amplitude:

$$VA = (x^2 + y^2 + z^2)^{\frac{1}{2}},$$

where x, y and z are simply those signals measured at the same time, squared, and square rooted, resulting in the length of the vector from the origin of the vector. Interconnecting the ends of vectors of successive measurements provides the trajectory of the successively measured vectors.

A simple transformation of the X-Y-Z axes signals through a Fast Fourier Transform allows to graph the information in the frequency domain. The resultant graphic of this power spectrum shows at what frequency the most power is being exhibited by the signal. This information along with spatial orientation and distance, plotted in three dimensions, gives information otherwise unobtainable by present means.

Thus far, all spatial information is preserved for reconstruction as a map. The Vector Amplitude (VA) measure provides information about how far from the center of the head the observed event is occurring; center of the head being the center (0,0,0) of the coordinate system.

The processing of digital data is accomplished in microseconds due to the use of digital signal processing (DSP) technology. This technology endows DSP devices to be programmed with the procedure described above. Thus, the examination procedure exists in software to be executed on a certain hardware configuration. The entire process takes place on a computer board connected to an IBM compatible computer. Because of the speed of the hardware, real time updating of the electrical phenomena in map form is ensured and allows advancement from snapshot diagnostics to real time "movie-like" mapping.

Therefore, by subjecting the brain to a probabilistic testing, averaging the electrical signals composing the response, the medical field has a tool to watch the brain as it processes information in dynamic form. In this procedure the response vectors sweep through the brain as a pattern from one area of the brain to another, both in serial and in parallel. If a trauma exists, the vectors will disappear from an expected particular area, and reappear when they have passed the inflicted area. The representation of the trauma is taken to be that area of the map left blank. This allows a diagnosis of the anthropometric extent of non-functions.

The length of a vector and its spatial orientation are also indicators of the processing of cognitive information- Thus, the pivoting of a vector refers to those areas of the brain used to process information not only at a neurophysiological level, but also at a neuropsychological level of cognitive awareness. In other terms, the tracking of cognitive phenomena are mapped as well. This arrangement of software and hardware is suited for the diagnosis of neurological and psychological defects such as stroke, Alzheimer's, coma, head injury, tumor, tissue damage, retardation, information deficit syndrome, and space perception deficit. These phenomena can be translated from analog-to-digital and mapped in a three dimensions coordinate system for real-time display purposes. Because of DSP technology, this mapping is qualitatively preserved as a movie, constantly changing as the brain processes information.

Equivalent results can be achieved by filtering the amplified analog brain signals, thereby eliminating all sudden changes in the amplitudes of the sensed signals.

Another application of the present invention, is its use as a monitor for the level of anesthesia a patient is under during surgery.

The length of the vector is dependent on the level of awareness. Its sweep complete, gives the path of the process. An incomplete sweep infers damage.

SHORT DESCRIPTION OF THE FIGURES

DESCRIPTION OF THE PREFERRED EMBODIMENT

Figure 1:
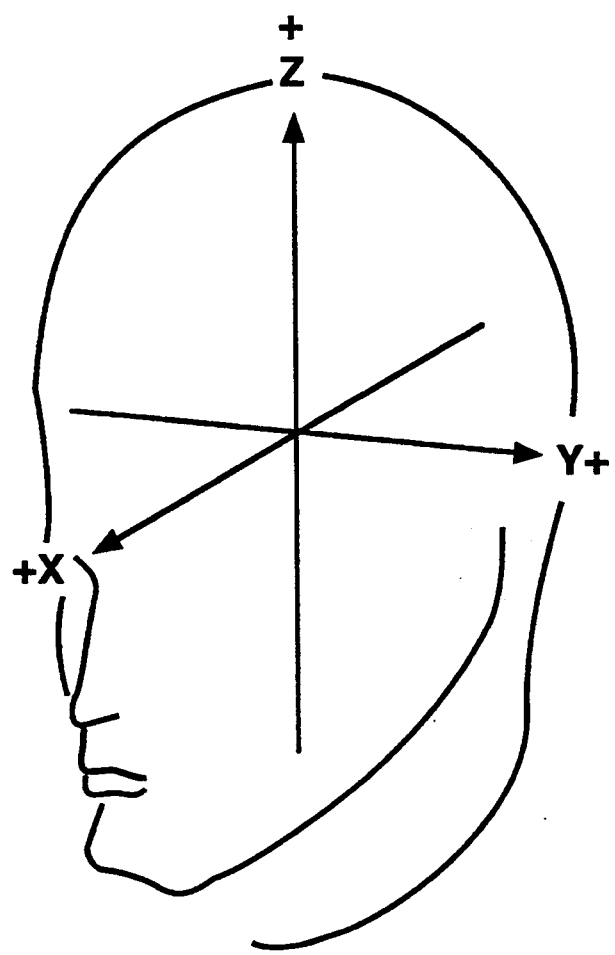
FIG. 1 is an illustration of a human head with a three dimensional cartesian coordinate system imposed.

FIG. 1 is an illustration of the human head with an imposed three-dimensional cartesian coordinate system and its orientation. To generate a three-dimensional image of the sensed signals in relation to the brain of the subject under examination, the orientation of the coordinate system for displaying the sensed signals has to be related to the location of the sensors attached to the head of the subject under examination.

nasion—inion=X-axis,
left—right mastoid=Y-axis, and
top of head to anterior throat=Z-axis.

The assignment of the polarity of the signals is indicated at each of the axes.

Figure 2:
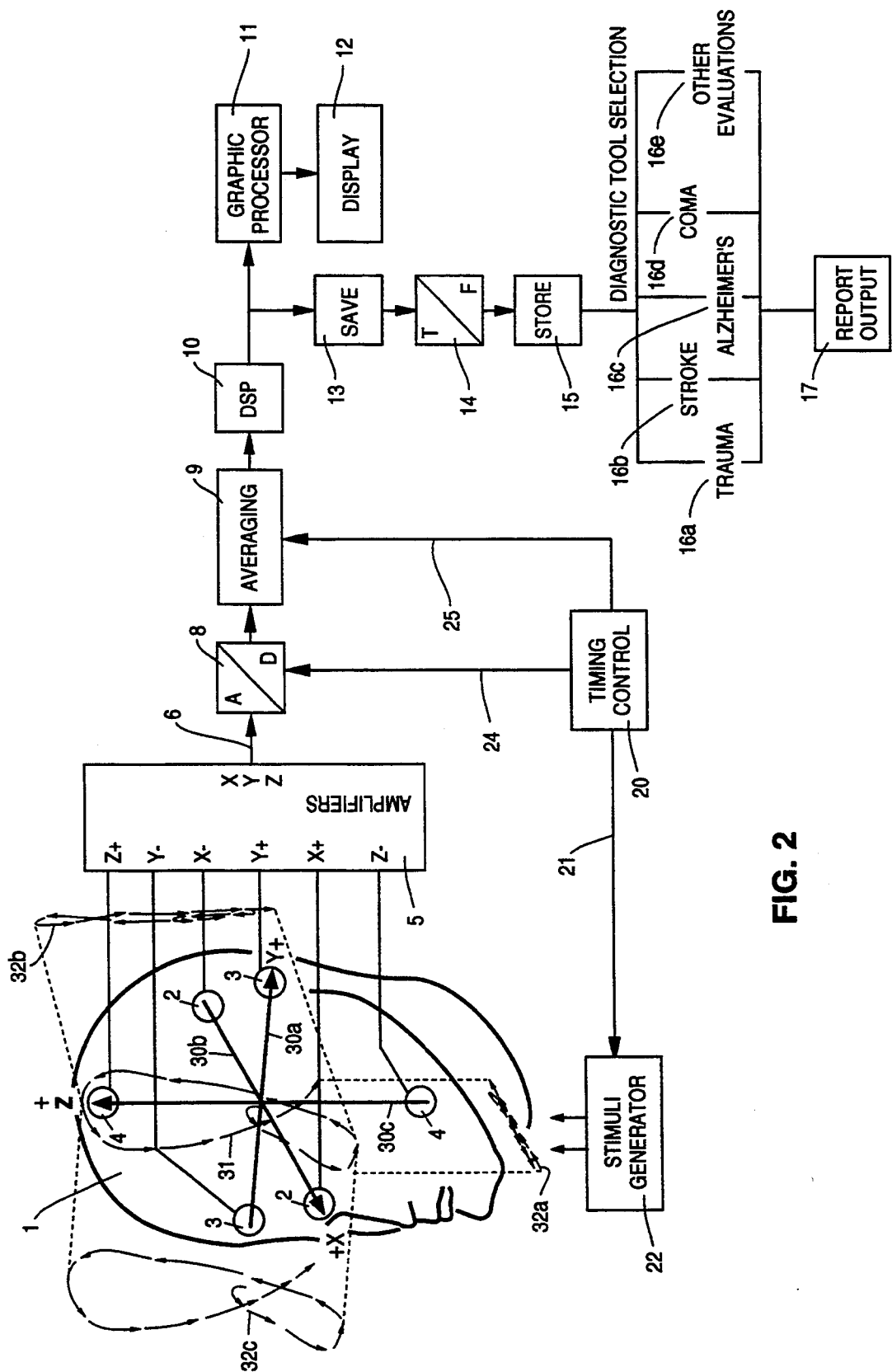
FIG. 2 is a schematic illustration of the apparatus for generating stimuli and processing of sensed signals.

FIG. 2 is a schematic diagram of the apparatus for sensing and processing electrical signals of the brain in response to sensory stimuli. The object of the examination 1 carries three pairs of electrical signal sensors 2, 3 and 4. Sensor pair 2 is mounted at inion and nasion, constituting the x-axis 30a. Sensor pair 3 is mounted at left and right mastoid (behind the ear), constituting the y-axis 30b. Sensor pair 4 is mounted on top of the head and at the anterior throat, constituting the z-axis 30c.

Each pair of sensors provides a differential signal which is amplified for further processing in amplifiers 5. The three amplified signals are supplied on line 6 to three analog-to-digital converters 8. Each one of the three digital signals is averaged by collecting sequences of successive values in averager 9 and determining the average value for the sequence. The averaged values are forwarded to digital signal processors 10 for mapping within a three-dimensional cartesian coordinate system.

The output signals of the digital signal processors 10 are supplied to graphic processor 11 which processes the signals for real-time display on monitor 12.

The output signals of digital signal processors 10 are also saved in memory 13 for further processing and evaluation. One such process 14 performs a Fast Fourier Transform on the signals stored in memory 13 to transfer the information into the frequency domain to determine frequency dependent parameters. The transformed information is store in memory 15. For evaluation of the gathered information the appropriate one of the provided diagnostic evaluation programs 16a thru 16e is selected. The selected one of the evaluation programs 16a thru 16e is applied to the gathered information and the results are output in a report 17.

A timing control 20 issues initiating signals on line 21 to stimuli signal generator 22 and on line 24 to analog-to-digital converter 8. Stimuli generator 22 issues stimuli signals in a sequence and fashion most suitable to an examination. Timing signals on line 24 determine at what time a response signal is to be sampled for conversion from analog to digital domain. Another timing signal on line 25 generated by timing control 20 controls the collating of successive digital response signal into groups of response signals for averaging.

Superimposed on head 1 and the three axes 30a, 30h, and 30c is a trajectory 31 of successively measured response vectors. Traces 32a, 32b, and 32c are projections of trajectory 31 on 3 planes X-Y, Y-Z, and X-Z.

As already indicated above, averager 9 may be supported or even substituted by filters which cuts off all signals above a given frequency. The three filters can be inserted in lines 6 between amplifiers 5 and analog-to-digital converters 8. Filters of this kind are well-known by the skilled artisan in this field. The use of a filter reduces sudden step-wise changes between successive averaged signals, if an averaged signals is not biased by the proceeding averaged value.

In FIG. 2 save-in--memory function 13 and store-in-memory function 15 may use independent memory modules or different sections of the same memory.

Figure 3:
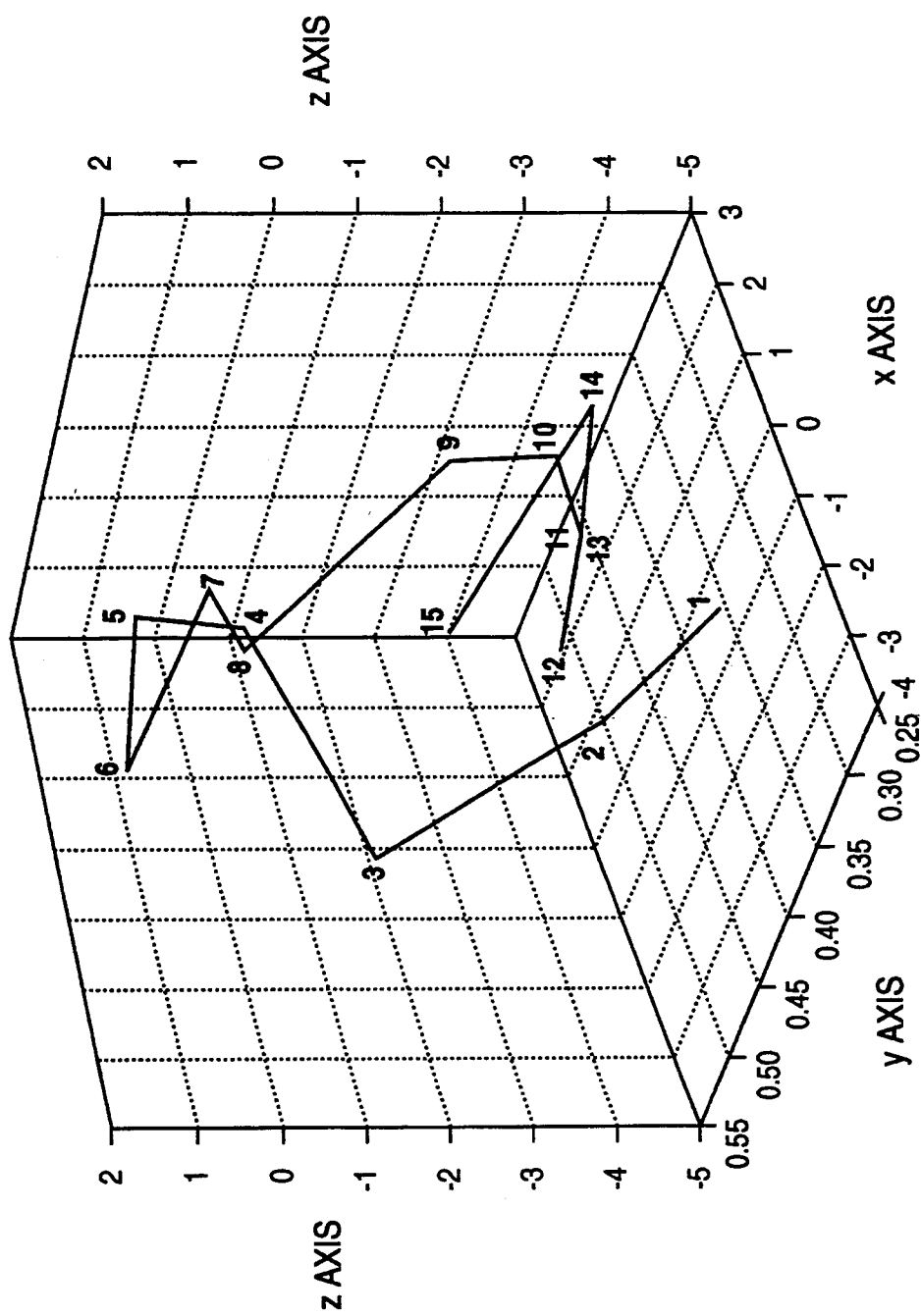
FIG. 3 is an illustration of a display showing the trajectory of successively collected response vectors.

In FIG. 3 the trajectory of successively measured response vectors are shown in a three-dimensional space. The time elapsed between numbered points on the trajectory is determined by time control 20; they are defined by the sampling of the analog response signal for analog-to-digital conversion and the number of digital data values used in an averaging process step. Time instances Pn and Nm and time periods Pn-Nm are measured from the time of the response causing stimuli. Selected time instances and time periods of special interest in the evaluation of the examination results may be highlighted by the display program of display processor 11.

By repetitively generating stimuli, one can follow the response signal sequence over time on the display in a movie-like fashion. Modifications in the generation of the stimuli can be more easily observed in their impact on the response signals than using staticly gathered response signals.

While the present invention is disclosed in an arrangement using an IBM compatible computer and an interface circuit to the analog sensors, it is considered to be within the expected capabilities of an artisan skilled in this field to adapt other computing means to fulfill the required operations by use of appropriate interface means and software.

I claim:

1. An apparatus for sensing and processing stimulated electrical brain signals of a subject under examination comprising
    means for generating stimulating signals;
    a group of three pairs of sensors adapted to be attached to the head of said subject under examination in planes substantially normal to each other for sensing differential electrical potentials between sensors of each of said pairs of sensors and providing electrical response signals,
        each of said pairs of sensors providing an orthogonal
    vector element of a triaxial response vector signal;
    timing means for initiating said stimulating signals and timing the processing of said response signals;
    processing means for receiving said electrical response signals and providing first output information representing sensed signals, and a triaxial response vector signal;
    a monitor operatively connected to said processing means for real time display of a plurality of trajectories of successively provided triaxial response vector signals; and
    evaluation means including a plurality of analysis means for selectively analyzing said first output information and outputting second output information representing the result of said selectively analyzed first output information.

2. An apparatus as claimed in claim 1, wherein said processing means include means for converting said electrical response signals into digital response data.

3. An apparatus as claimed in claim 2, wherein said processing means further include averaging means for averaging the values of a predetermined number of successive ones of said digital response data.

4. An apparatus as claimed in claim 1 wherein each of said pairs of sensors define an axis, the so defined three axes being substantially normal to each other, and
    said electrical response signals constitute axes related electrical response signals.

5. An apparatus as claimed in claim 4, wherein said processing means assemble said response signals to a vector in a three-dimensional space and provide timed trajectory information for the end of said vector.

6. An apparatus as claimed in claim 4, wherein said processing means include a differential amplifier for each one of said pairs of sensors for amplifying said response signal and providing an axis related signal for further use in said processing means.

7. A method for real-time mapping of evoked potentials representing brain activities of a subject under examination comprising the steps of
    generating a sequence of stimulating signals for said subject under examination; gathering a plurality of orthogonally oriented sensory
    data signals from said subject under examination;
    averaging said sensory data signals over predetermined time periods and providing averaged data signals;
    processing said averaged data signals and generating a triaxial vector signal for real-time display in a three-dimensional coordinate system;
    displaying and mapping a plurality of trajectories of successively provided triaxial vector signals;
    storing said averaged data signals in storage means thereby making said averaged data available for processing at a later time; and
    evaluating said stored data signals using a selected one of a plurality of evaluation criteria.

8. A method for real-time mapping of a plurality of evoked response signals representing brain activities of a subject under examination comprising the steps of
    generating a sequence of stimulating signals for said subject under examination;
    generating timing signals for initiating said stimulating signals;
    sensing said plurality of response signals, each of said response signal representing a vector element of a triaxial activity vector;
    sampling each one of said response data signals at determined time intervals relative to said sequence of stimulating signals and converting each one of said plurality of sensed data signals to digital data;
    averaging said digital data over a predetermined number of said time intervals;
    processing said averaged digital data to provide real-time triaxial data vectors;
    displaying said real-time triaxial data vectors in a selected triaxial coordinate system, thereby displaying a time-wise trajectory of said triaxial data vector;

displaying and mapping a plurality of trajectories of successively provided triaxial vector signals;

storing said real-time data thereby making said real-time data available for evaluation at a later time;

applying a fast fourier transform operation to said real-time data for generating frequency domain data;

evaluating said frequency domain data using a selected one of a plurality of evaluation processes; and providing an output including data on said selected evaluation process.

* * * * *